United States Patent [19]

Lyons, III

[11] Patent Number: 4,499,899
[45] Date of Patent: Feb. 19, 1985

[54] FIBER-OPTIC ILLUMINATED MICROSURGICAL SCISSORS

[75] Inventor: William G. Lyons, III, Wilbraham, Mass.

[73] Assignee: Brimfield Precision, Inc., Brimfield, Mass.

[21] Appl. No.: 509,780

[22] Filed: Jun. 30, 1983

Related U.S. Application Data

[63] Continuation-in-part of Ser. No. 459,949, Jan. 21, 1983.

[51] Int. Cl.³ .............................................. A61B 17/32
[52] U.S. Cl. ........................................ 128/305; 128/6; 128/318
[58] Field of Search ..................... 128/305, 305.1, 318, 128/312, 321, 319, 320, 309, 303.15, 6, 303 A; 30/240, 189

[56] References Cited

U.S. PATENT DOCUMENTS

| | | | |
|---|---|---|---|
| 2,106,575 | 1/1938 | Moore | 128/309 |
| 2,790,437 | 4/1957 | Moore | 128/321 X |
| 2,894,324 | 7/1959 | Hardin | 30/240 |
| 3,790,048 | 2/1974 | Luciano et al. | 604/211 |
| 3,945,375 | 3/1976 | Banko | 128/6 |
| 4,027,510 | 6/1977 | Hiltebrandt | 128/6 X |
| 4,257,420 | 3/1981 | Terayama | 128/303 A |
| 4,362,160 | 12/1982 | Hiltebrandt | 128/303.15 |

FOREIGN PATENT DOCUMENTS

| | | | |
|---|---|---|---|
| 3668 | 8/1979 | European Pat. Off. | 128/318 |
| 2921093 | 11/1980 | Fed. Rep. of Germany | 128/346 |
| 3122 | 11/1981 | Int'l Pat. Institute | 128/318 |

*Primary Examiner*—Michael H. Thaler
*Attorney, Agent, or Firm*—Donald S. Holland

[57] ABSTRACT

A rotary cutting scissors for microsurgery is disclosed. The rotary scissors instrument comprises a pair of scissor blades mounted on an end of a shaft assembly for snipping away soft tissue during surgery wherein the other end of the shaft assembly is mounted within a spring-loaded rongeur handle that is adapted to be comfortably grasped by the cupped hand of a user. When the handle is squeezed, a helical drive mechanism housed in an upper portion of the handle is actuated to rotate one of the scissor blades against the other so as to cause the desired snipping action.

The instrument further comprises an internal fiber-optic light source that emits a bright light near the scissor blades during surgery to illuminate the area being operated on so that the surgeon can see precisely what he is dealing with and thereby avoid mistakes. This light constantly illuminates the line of cut by moving in tandem with the instrument during surgery.

4 Claims, 5 Drawing Figures

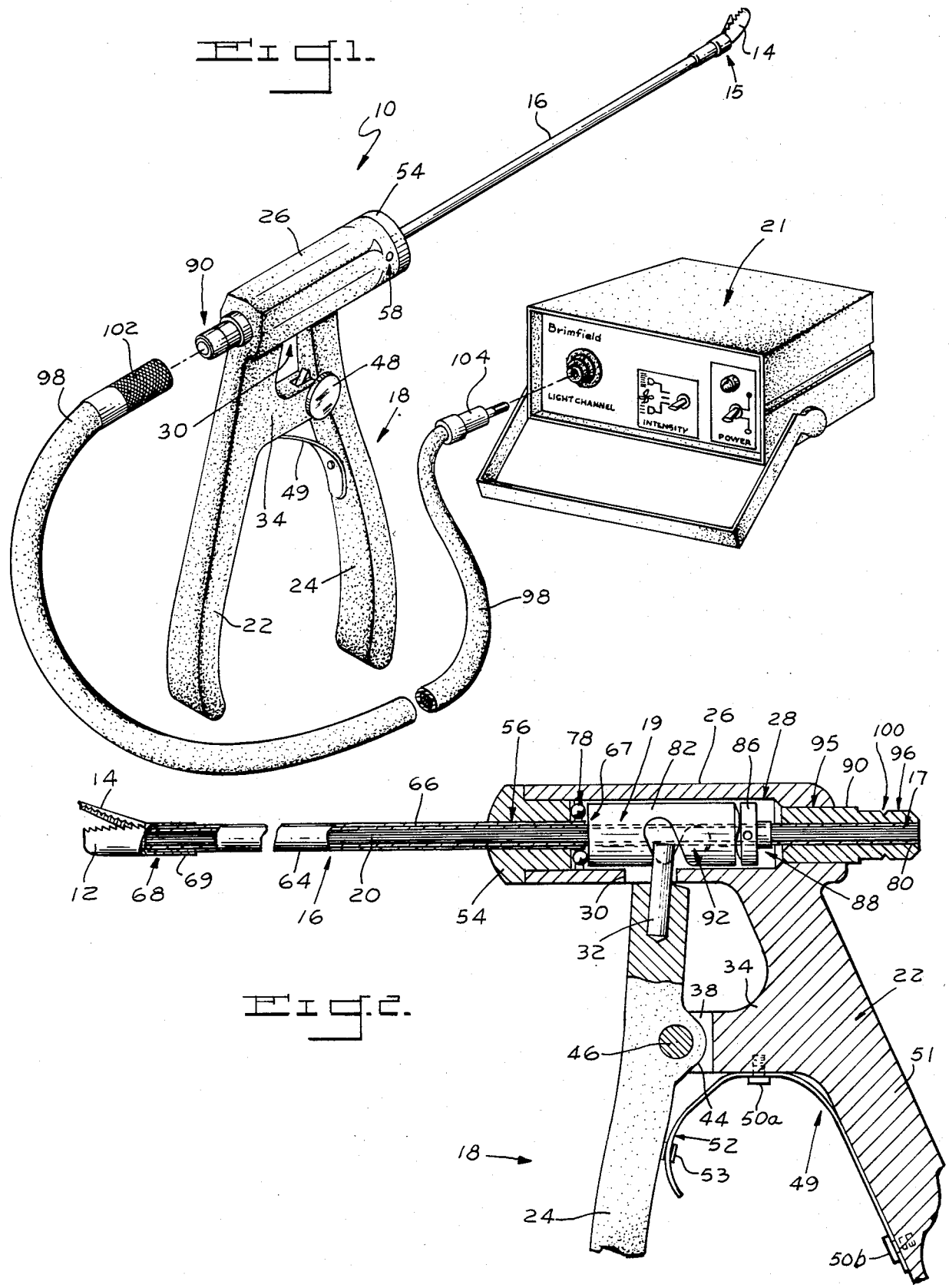

FIBER-OPTIC ILLUMINATED MICROSURGICAL SCISSORS

RELATED APPLICATIONS

This application is a continuation-in-part of U.S. patent application, Ser. No. 459,949, filed Jan. 21, 1983, entitled "ROTARY CUTTING SCISSORS FOR SURGERY" and assigned to the same assignee.

BACKGROUND OF THE INVENTION

This invention relates to surgical instruments and, more particularly, relates to rotary cutting scissors used in removing soft tissue during microsurgery, such as arthroscopy.

In arthroscopic surgery, torn soft tissue in the knee is cut away to allow the knee to mend. Often, during athletic events, a participant will twist his knee in an awkward position such that he tears soft meniscus tissue within it. In order to repair the knee, it is sometimes necessary for a surgeon to remove the jagged portion of the tear and then go back and round the remaining marginal edge of the previously torn section. Otherwise, the tear will continue to rip and cause further damage. If the tear is removed, the damage is halted and the remaining tissue in the area of the tear is able to rejuvenate; the rounded edge of the cut tissue grows "outwardly" and knits with adjacent, undamaged tissue.

Recently, tiny, hand-held rotary cutting scissors have been introduced to enable a surgeon to more easily and surely cut away the toughest and most resistant cartilage and tissue. These prior devices, such as the ACUFEX ® rotary cutting scissors, manufactured by Acufex Microsurgical, Inc., consist of a rotary scissor assembly mounted at the end of a tiny shaft assembly so as to enable the surgeon to reach extreme posterior and anterior portions of the knee joint to increase cutting accuracy.

The ACUFEX ® scissor assembly consists of a pair of angularly offset scissor blades that can be serrated. One of the blades is fixedly mounted on an end of a stationary outer tube of the aforementioned shaft assembly. The other is fixedly mounted on an adjacent end of a concentric inner rod which is telescopically located within the outer tube and mounted for rotation therein by a cylindrical handle that supports the opposite end of the rod in a cantilevered fashion. The handle is parallel to both the inner rod and outer tube and includes a spring-loaded, thumb-squeezed plunger for rotatably driving the inner rod.

By pushing down on the plunger with his thumb, the surgeon activates a "rack-and-pinion" gearing to rotate the inner rod, which in turn causes the scissor blade attached to it to rotate through a surface of revolution adjacent the fixedly mounted, stationary scissor blade. This produces a cutting surface between the mating scissor surfaces and enables the surgeon to cut away the damaged tissue.

While the ACUFEX ® device is useful, a major problem exists with it. Due to the drive mechanism being situated in a cylinder and its being actuated by a thumb-squeezing movement, the depth of the cut performed with this device is hard to control. The natural inclination of the user of this device is to tip or tilt the scissor end downwardly each time the the thumb is pushed down to actuate the device's plunger. Therefore, a surgeon has to consciously think about this problem and apply an awkward counter pressure to the bottom of the cylindrical handle which causes discomfort and subsequent fatigue.

While such fatigue may not matter if a doctor performs only one operation in a day since the doctor's hand has time to recuperate, it is a genuine concern when the doctor is in the midst of his third or fourth operation of the day, especially for the patient. The doctor's cutting accuracy may be decreased due to this fatigue.

Another problem that occurs with the ACUFEX ® scissors, and other cutting tools as well, is the need for proper lighting near their cutting tips during surgery. During an operation, it is extremely important that the area being operated on be constantly illuminated so that the surgeon can see precisely what he is dealing with and thereby avoid mistakes.

While there are some portable fiber-optic light sources that are presently being used to illuminate the general cutting area during surgery, they are usually headlights mounted on a "coal-miner" type helmet or a headband worn by the surgeon, such as the headband shown in U.S. Pat. No. 3,285,242 to Wallace. Although this type of light sources is somewhat beneficial, it is useful to only a limited extent because it is attached to the "helmet" and does not move in tandem with the constantly moving tip of the cutting instrument (here, the scissors) during surgery. In order to re-aim the light, the light source has to be pivoted on the helmet or the surgeon has to cock his head. Further, by the time that the light beam reaches the cutting area, it becomes diffused due to the distance between the helmet and the cutting area.

Accordingly, it is the primary object of the present invention to provide an improved rotary cutting scissors for surgery in which the undesirable characteristics of the prior art are overcome.

It is a more specific object to provide a rotary cutting scissors with a new handle configuration and drive mechanism that does away with the problem of thumb fatigue found in the prior art.

It is another object to provide an improved rotary cutting tool that allows the user to more easily control the depth of his cut with the device.

It is a further object to provide an improved rotary cutting scissors that does not jam as easily as the prior art. In the prior art, there is a problem of separating the scissor edges when they become wedged together during the cutting of an extremely tough piece of tissue.

It is yet another object to provide an improved rotary cutting scissors in which the operating surgeon is able to keep the tip steady during the cutting in a precise perpendicular angle to the line of cut.

It is another object to provide an improved rotary cutting scissors in particular, and other surgical cutting tools in general, with a concentrated light source that brightly illuminates the line of cut and moves with the tool's "cutting edge" during surgery.

It is a more specific object to provide an improved rotary cutting scissors with an innovative, internal fiber-optic light source that emits a bright light near the cutting line of the scissor blades during surgery, wherein the light constantly illuminates the area being cut by moving in tandem with the instrument during its constant shifting in surgery.

It is still another object to provide an improved rotary cutting scissors that is simple and economical in design, yet sturdy and effective to use.

BRIEF DESCRIPTION OF THE DRAWINGS

With the foregoing background and objectives of the invention in mind, reference is made to the accompanying drawings, in which:

FIG. 1 is a perspective view of a surgical instrument or rotary cutting scissors constructed in accordance with the present invention. It also includes perspective views of a portable fiber-optic light source and a fiber-optic cable, partially broken away, for connecting the surgical instrument to the light source;

FIG. 2 is a side-elevational view of the surgical instrument of FIG. 1, partly in cross section, showing a fiber-optic bundle running through the instrument;

DETAILED DESCRIPTION OF THE PREFERRED EMBODIMENT

Figure 3:
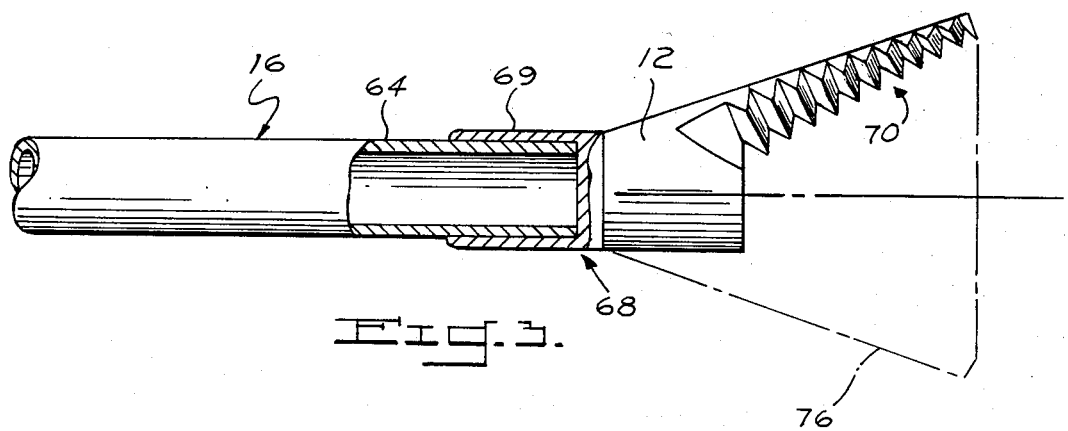
FIG. 3 is an enlarged, cross-sectional view of the instrument's outer scissor tip assembly shown in FIG. 1.

Referring to the drawings in detail, a novel rotary cutting scissors for surgery is shown and generally designated by the reference numeral 10. The rotary scissors instrument basically comprises a pair of scissor blades 12, 14 mounted on an end 15 of a shaft assembly 16 for snipping away soft tissue during the surgery, wherein the other end 17 of the shaft assembly is mounted within a spring-loaded rongeur handle 18 that is adapted to be grasped by the cupped hand (not shown) of a user. When the handle is squeezed, a helical drive mechanism 19 housed in the handle is actuated to rotate one of the scissor blades (14) against the other (12) so as to cause the desired snipping action.

Further, the rotary cutting scissors also basically comprises a fiber-optic bundle 20 housed within the center of the shaft assembly 16. It is used to transmit a concentrated light from any suitable fiber-optic light source 21 to the scissor end 15 during surgery. The light emanates from the end 15 and brightly illuminates the precise area being operated on by the scissor blades 12, 14.

As shown in FIGS. 1 and 2, the handle 18 is a modified version of conventional "surgical" handles whose general configurations are known as rongeur handles to those skilled in the surgical instrument art.

The instrument's handle 18 includes a substantially F-shaped rear body 22 to which a cutter trigger 24 is pivotally attached. The upper stem 26 of the "F" has a horizontal bore or channel 28 for housing the drive mechanism 19, and the underside of that stem has a longitudinally-extending slot 30 through which a finger portion 32 of the cutter trigger 24 extends to drive the mechanism 19 when the trigger is squeezed.

The lower stem 34 of the "F" includes a pair of ears (one shown at 38) with cross holes for pivotally attaching the cutter trigger 24 to the handle 18. A lug 44 extends from the rear of the trigger and fits between the ears. It is held in place for rotation thereon by any suitable trunnion pin 46 (here, the crossbar of a standard blind fastener 48) that fits between the ears' cross holes and through an aligned bore in the lug 44. In the preferred embodiment, the blind fastener has male and female T-shaped members whose stems are press fit together so as to be fixed in place.

The trigger 24 is normally biased toward its fully-extended position shown in FIG. 1 by a U-shaped leaf spring 49 that is attached by two screws 50a, 50b, to the underside of the lower "F" stem 34 and the front of the vertical portion 51 of the "F". The spring 49 has a front portion 52 which is positioned against or closely adjacent to the rear face of the trigger so as to provide the biasing. In the preferred embodiment, a plastic "rivet" 53 is press fit through a hole in the spring's front portion 52 and acts as a slidable cushion between the spring and the trigger's rear face during operation of the instrument 10.

To provide a comfortable grip, the vertical portion 51 of the "F" of the rear body 22 and the lower portion of cutter trigger 24 are arcuately shaped so that the arcuate portions oppose one another when the instrument 10 is in its assembled position.

Referring to FIG. 2, the shaft assembly 16 for the scissor blades is mounted by its end 17 extending into the horizontal bore 28 of the rear body 22. It is basically held in a cantilevered position by a mushroom-shaped nose piece or end cap 54. The cap 54 has a through bore 56 into which the shaft assembly extends, and the cap is fixed in a stationary position within the rear body 22 by a pair of set screws (one shown at 58) that fit through holes on opposite sides of the body 22 and into aligned indentations on opposite sides of the cap 54.

The shaft assembly 16 consists of an outer tube 64 and a concentric, hollow inner rod 66 that is mounted for rotation within the tube. One end 67 of the outer tube 64 extends through the bore 56 of end cap 54 and is held stationary by any suitable means (here, an epoxy glue). At the opposite end 68 of the outer tube, one of the scissor blades (12) is mounted in a fixed position by an integral sleeve 69 of the blade that fits over the end and which is secured by any suitable means, such as soldering (see FIG. 3).

Figure 4:
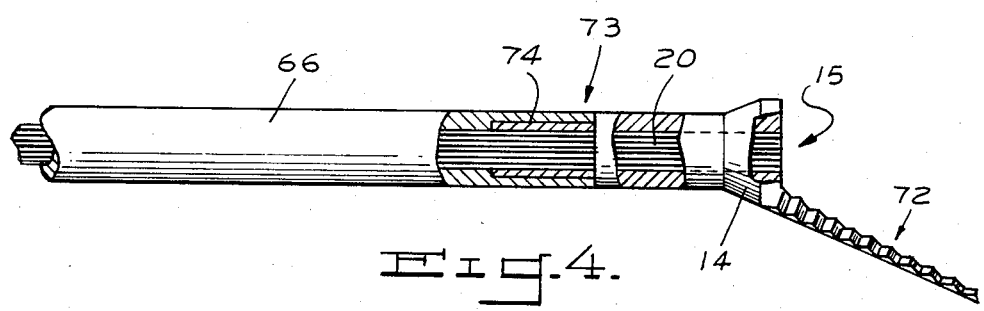
FIG. 4 is an enlarged, cross-sectional view of an inner scissor tip assembly for the instrument shown in FIG. 1; and, FIG. 5 is a perspective view of the inner scissor tip assembly with an added phantom illustration to show the movement of this tip during cutting with the instrument.
Figure 5:
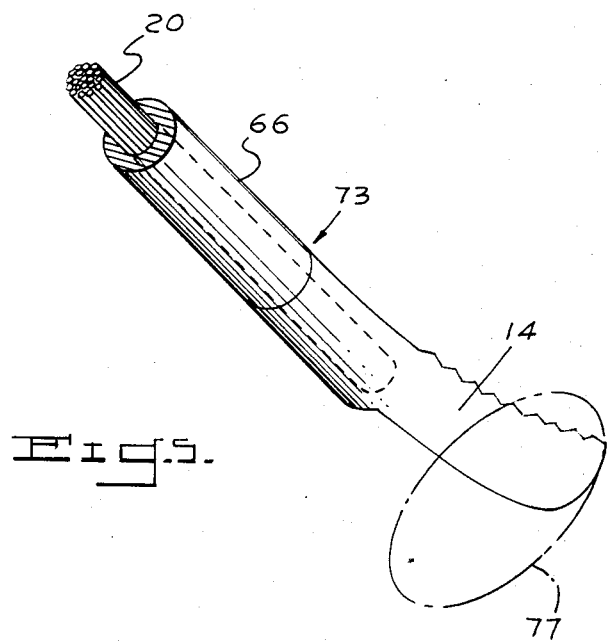

Scissor blade 12 is angularly offset from the axis of the outer tube 64 and includes a sharp, serrated cutting edge 70 for mating with a complementary edge 72 of the other scissor blade 14. The scissor blade 14 is mounted on an end 73 of the inner rod 66 by a stub shaft 74 that fits into and is held in a complementary channel in the rod by any suitable means, such as brazing (see FIG. 4). Like blade 12, the blade 14 is angularly offset from the end 73 of inner rod 66, so that when blade 14 is rotated by the drive mechanism 19, the blade 14 moves in a conical surface of revolution 76 and the cutting edges 70, 72 mate. The path of the tip of blade 14 is shown in FIG. 5 and designated by the reference numeral 77.

Though not shown, both blades 12, 14 can have flat edges instead of the illustrated serrated edges 70, 72. Further, the blades can be slightly curved or hooked, instead of being straight as illustrated.

Referring now to FIG. 2, the helical drive mechanism 19 is attached to the end 17 of shaft assembly 16. The mechanism comprises (as viewed from left to right in FIG. 2) a ball bushing 78 for rotatably supporting an end 80 of inner rod 66 which extends through the center of the bushing, a cylinder 82 with a hollow core through which rod end 80 extends, a substantially circular spring retainer 86 that fits in an end of the core and which is keyed to the cylinder for rotation therewith. The retainer 86 has a central bore through which rod end 80 further extends and the retainer is spot welded to the rod at 88 (on the opposite side from its "keyed" connection to the cylinder) so that the rod will rotate with the cylinder and retainer. The end 80 extends from the retainer into a through bore of a standard fiber-optic cable fitting 90, which is fixedly attached to the rear body 22, so that the end 80 is freely supported for rotation inside the stationary fitting 90.

Cylinder 82 has a left-handed helical groove or furrow 92 into which finger portion 32 of the cutter trigger 24 extends. As the lower portion of the trigger is squeezed, the trigger pivots on trunnion pin 46 and its finger portion 32 moves forward (right to left as viewed in FIG. 2) in slot 30 of the upper stem 26 of the "F" in rear body 22. As the finger moves forward, it cooperates with the helical groove 92 to cause the cylinder 82 to rotate in a counterclockwise movement. Since the end 80 of inner rod 66 is fixedly connected to the cylinder by the retainer 86, the inner rod rotates with the cylinder and causes the cutting edge 70 of the scissor blade 14 to rotate against the complementary edge 72 of the stationary scissor blade 12. This produces a precise snipping action.

As the user uncups his grip, the leaf spring 49 biases the trigger 24 back to its original position and causes the blade 14 to move away from 12 in a reciprocal movement. By alternately squeezing and loosening his grip, a user can precisely cause the blades to move in a to-and-fro action relative to one another, thereby producing a controlled snipping action for cutting away undesired tissue.

Unlike the prior art, if the scissor blades 12, 14 become jammed during cutting of an extremely tough piece of tissue, the situation is easy to overcome. The user of the invention merely places the back of his cupped fingers against the rear face of the trigger 24 and pushes his fingers outwardly. This causes the trigger 24 to move and the drive mechanism 19 to open the blades and free them from the tissue.

In the preferred embodiment, the handle 18 is made of anodized aluminum for durability and ease of handling. Since the handle is light and comfortably configured, a user can keep the cutting end of the instrument perpendicular to the desired line of cut. Further, the comfortable curvature of the handle allows the pressure utilized in squeezing to be distributed over the user's entire hand, thereby preventing the hand cramps and fatigue caused by prior rotary cutting devices that utilized the thumb-actuated plunger.

As best shown in FIG. 2, the fiber-optic bundle 20 is contained with the hollow inner rod 66 and is movable with it. The bundle runs the length of the rod and is epoxied and polished at ends 15, 80 in the traditional manner of securement for fiber-optic bundles in general. Since the bundle is fixed to the rod, it rotates with the rod during the snipping action produced by manipulating the handle.

The fitting 90 in which end 80 of the rod 66 rotates has a right-cylindrical end portion 95 that fits into a complementary bore in the rear of body 22. This end portion extends outwardly from the body so as to support an opposite, cylindrical end portion 96 in a cantilevered position for its attachment to a standard fiber-optic cable 98. The cantilevered portion 96 has a slightly smaller diameter than portion 95 and has an annular notch 100 along its mid-length for detachably connecting a snap-connector end 102 of the cable 98.

By hooking up the snap-connector end to the fitting 90 and then attaching an opposite plug end 104 of the cable to the light source 21 (here, a portable BRIMFIELD ® U.S.-1000 fiber-optic light source manufactured by Brimfield Scientific Instruments), a user can transmit fiber-optic light from the source to scissor end 15 of the shaft assembly 16 during surgery.

The light that emanates from end 15 shines directly on the area being operated on so that the surgeon can see exactly what he is dealing with and thereby avoid mistakes. Since the light emanates at a point closely adjacent the cutting area, it is highly concentrated and is not diffused to the extent found in the prior art, such as U.S. Pat. No. 3,285,242 described in this application's section entitled "BACKGROUND OF THE INVENTION". Further, since the fiber-optic bundle 20 is carried by the rod 66, it automatically moves in tandem with the line of cut during any realignment of the instrument 10 during surgery. This insures that the cutting area will always be properly lighted.

In the preferred embodiment, the cable fitting 90 is normally manufactured to conform to the specifications of the fitting most used by the industry, namely, the ACMI fitting manufactured by American Cystoscope Makers, Inc. Its size and shape can, of course, be adapted to fit the fiber-optic cable of any equipment that the particular user owns.

While a few design options have been expressly disclosed, it should be understood by those skilled in the art that other structural modifications can be made without departing from the spirit of the invention. For example, while the preferred handle 18 is made of metal for durability, it can be made of plastic for further lightness in handling the instrument. Accordingly, reference should be made primarily to the accompanying claims, rather than to the specification, to determine the scope of the invention.

Having thus described the invention, what is claimed is:

1. A rotary cutting scissors for surgery, said scissors comprising:
  (a) a pair of scissor blades mounted on an end of a shaft assembly for snipping away tissue during the surgery;
  (b) said shaft assembly having an outer tube and a concentric inner rod telescopically mounted therein, wherein one of the tube and rod members is held stationary while the other is mounted for rotation relative to the stationary member without axial movement relative thereto, and one of the scissor blades is mounted in a fixed, angularly offset position on an end of the inner rod while the other blade is fixedly mounted in an opposed, angularly offset position on an adjacent end of the outer tube;
  (c) said shaft assembly having an opposite end mounted within a longitudinally-extending bore of a spring-loaded rongeur handle that is adapted to be grasped by the cupped hand of a user, said handle having a generally F-shaped rear body wherein the upper, substantially horizontal stem of the "F" contains the bore and the lower stem has a front trigger pivotally attached to it, said trigger having a finger that extends through a longitudinally-extending slot in the upper portion and into the bore where the finger moves relative to the bore as the trigger is squeezed and released by the user;
  (d) a helical drive means housed in the bore of the rear body to rotate said rotatable one of the tube and rod members relative to said stationary one of the members and thereby cause the scissor blade fixed on said rotatable member to rotate against the other scissor blade fixed on said stationary member, while the two members remain substantially axially stationary relative to each other, so that a cutting surface on one of the blades mates with a complementary cutting surface on the other blade to produce a snipping action, said drive means including a gear fixedly attached to said rotatable one of the tube and rod members wherein the gear includes a helical groove on its periphery that engages the finger of the trigger so that the groove cooperates with the finger, as the trigger is being squeezed and released, and the finger moves in the slot to rotate the blades relative to one another, and wherein the entire drive means housed in said bore, except for the finger, remains axially stationary relative to the members while the blades are being rotated;

(e) means for emitting a fiber-optic light near the scissor blades during surgery to brightly illuminate the line of cut produced by the blades, wherein the lighting means moves in tandem with the longitudinal axis of the shaft assembly to constantly illuminate the line of cut during shifting of the axis in the surgery; and, (f) wherein the inner rod is hollow with a longitudinal through bore and the lighting means comprises a fiber-optic bundle that substantially fills the bore and is secured to both ends of it.

2. The rotary cutting scissors of claim 1 wherein the opposite end of the inner rod from its scissor blade end is journaled for rotation inside a through bore of a fiber-optic fitting that is fixedly attached to the rear body, said fitting having one end extending into the bore of the upper portion of the handle and an opposite end extending from the upper portion in a cantilevered manner where it is adapted to be attached to a fiber-optic light source for transmitting fiber-optic light through the bundle and out the scissor blade end of the inner rod.

3. A rotary cutting scissors for surgery, said scissors comprising:
(a) a pair of scissor blades mounted on an end of a shaft assembly for snipping away tissue during the surgery;
(b) said shaft assembly having an outer tube and a concentric inner rod telescopically mounted for rotation therein while remaining axially stationary relative to the outer tube, wherein one of the scissor blades is mounted in a fixed, angularly offset position on an end of the inner rod while the other blade is fixedly mounted in an opposed, angularly offset position on an adjacent end of the outer tube;
(c) said shaft assembly and said outer tube and said inner rod each having an opposite end mounted within a longitudinally-extending bore of a spring-loaded rongeur handle that is adapted to be grasped by the cupped hand of a user, said handle having a rear body with an upper portion that contains the bore and the front trigger pivotally attached to the rear body, wherein the trigger has a finger that extends through a longitudinally-extending slot in the upper portion and into the bore where the finger moves relative to the bore as the trigger is squeezed and released by the user;
(d) wherein said outer tube is fixed relative to the handle;
(e) a helical drive means housed in the bore of the rear body to rotate the inner rod relative to the outer tube and cause the scissor blade attached to the inner rod to rotate against the other scissor blade attached to the fixed outer tube, while the inner rod and outer tube remain substantially axially stationary relative to each other, so that a cutting surface on one of the blades mates with a complementary cutting surface on the other blade to produce a snipping action, said drive means including a gear fixedly attached to the inner rod wherein the gear includes a helical groove on its periphery that engages the finger of the trigger so that the groove cooperates with the finger, as the trigger is being squeezed and released, and the finger moves in the slot to rotate the inner rod and thereby rotate its attached scissor blade relative to the scissor blade of the outer tube, and wherein the entire the drive means housed is said bore, except for the finger, remains axially stationary relative to the members while the blades are being rotated;

(f) means for emitting a fiber-optic light near the scissor blades during surgery to brightly illuminate the line of cut produced by the blades, wherein the lighting means moves in tandem with the longitudinal axis of the shaft assembly to constantly illuminate the line of cut during shifting of the axis in the surgery; and, (g) wherein the inner rod is hollow with a central through bore and the lighting means comprises a fiber-optic bundle that substantially fills the bore and is secured to both ends of it.

4. The rotary cutting scissors of claim 3 wherein the opposite end of the inner rod from its scissor blade end is journaled for rotation inside a through bore of a fiber-optic fitting that is fixedly attached to the rear body, said fitting having one end extending into the bore of the upper portion of the handle and an opposite end extending from the upper portion in a cantilevered manner where it is adapted to be attached to a fiber-optic light source for transmitting fiber-optic light through the bundle and out the scissor blade end of the inner rod.

* * * * *